(12) United States Patent
Spivak

(10) Patent No.: US 6,838,585 B2
(45) Date of Patent: Jan. 4, 2005

(54) PALLADIUM-CATALYZED CROSS-COUPLING OF ARYLDIAZONIUM SALTS WITH ARYLSILANES

(75) Inventor: David A. Spivak, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 330 days.

(21) Appl. No.: 10/005,664

(22) Filed: Nov. 8, 2001

(65) Prior Publication Data
US 2003/0120124 A1 Jun. 26, 2003

(51) Int. Cl.[7] .............................................. C07C 15/12
(52) U.S. Cl. .............................. 585/25; 585/24; 585/26; 585/27; 585/454; 585/469; 585/470; 585/471
(58) Field of Search ............................... 585/24, 25, 26, 585/27, 454, 470, 471, 469

(56) References Cited

PUBLICATIONS

Hatanaka, Y. et al., "Selective synthesis of unsymmetrical biaryls via palladium–catalyzed cross–coupling of arylfluorosilanes with aryl iodides," Chem. Lett. 1989, pp. 1711–1714, no month.

Hiyama, T., "Organosilicon compounds in cross–coupling reactions," pp. 421–453 in F. Diederich et al. (Eds.), Metal–Catalyzed Cross–Coupling Reactions (Wiley–VCH Verlag 1998), no month.

Ikenaga, K. et al., "Reaction of diazonium salts with transition metals. Part 11. Palladium–catalyzed aryldesilylation of alkenylsilanes by arenediazonium salts," J. Chem. Soc. Perkin Trans. 1986, pp. 1959–1964.

Kikukawa, K. et al., "Reaction of diazonium salts with transition Metals. IX, Reaction of vinyltrimethylsilane with arenediazonium tetrafluoroborates under palladium(0) catalysis," J. Organomet. Chem., vol. 270, pp. 277–282 (1984).

Spivak, D. and Simon, R., "Palladium catalyzed cross–coupling of silyl enol–ethers with arenediazonium salts," Poster presented at Apr. 1–5, 2001 meeting of the American Chemical Society, San Diego, CA.

Spivak, D. and Simon, R., "Palladium catalyzed cross–coupling of silyl enol–ethers with arenediazonium salts," Abstract of poster presented at Apr. 1–5, 2001 meeting of the American Chemical Society, San Diego, CA (abstract mailed to meeting participants approximately Feb. or Mar. 2001).

*Primary Examiner*—Elizabeth D. Wood
(74) *Attorney, Agent, or Firm*—John H. Runnels

(57) ABSTRACT

A palladium catalyzed cross-coupling of aryldiazonium salts with organosilanes is disclosed. New reactions that are user friendly and environmentally friendly are now possible, including some reactions that could not be achieved using prior methods. The organosilanes that may be cross-coupled with aryldiazonium salts include, for example, Ar'—Si(L)$_3$, where Ar'=aryl, and where L=CH$_3$, OCH$_3$, F, Cl, R, or OR.

9 Claims, No Drawings

PALLADIUM-CATALYZED CROSS-COUPLING OF ARYLDIAZONIUM SALTS WITH ARYLSILANES

This invention pertains to the cross-coupling of aromatic compounds, particularly to the palladium-catalyzed cross-coupling of aryidiazonium salts with arylsilanes.

Cross-coupling reactions are one way to form carbon-carbon bonds, linking two groups together in the generic reaction

where X and Y are co-called "leaving groups."

Cross-coupling reactions are powerful tools for the synthesis of pharmaceuticals, dyes and pigments, agrochemicals, electronic materials, optical materials, conjugated polymers, and other organic compounds.

One example is the so-called Heck cross-coupling of aryl or alkenyl halides with alkenes, whose mechanism is shown in scheme 1. The three principal mechanistic steps are: (1) the oxidative addition of Pd(0) to the aryl or alkenyl halide; (2) syn-addition of the aryl σ-alkenyl/aryl palladium bond to the double bond of the reaction alkene; and (3) reductive elimination to form the cross-coupled product and regenerate the palladium catalyst.

Scheme 1.
Catalytic cycle for the Heck cross-coupling reaction.

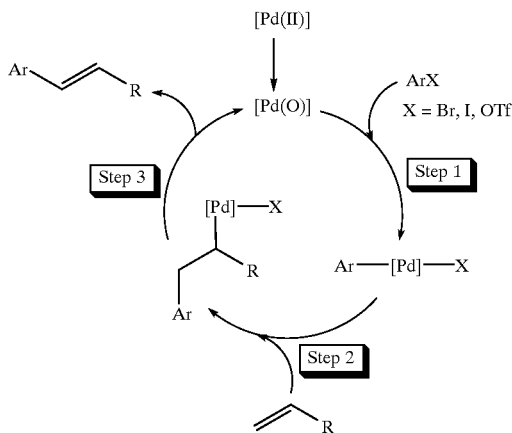

A mechanistically similar method for obtaining cross-coupled products is shown in scheme 2. Here, an organometallic reagent is used in the second step instead of an alkene to produce a bis(organo)palladium(II) intermediate via transmetallation, which then undergoes rapid reductive elimination to yield the cross-coupled product(s).

Scheme 2.
Catalytic cycle for the cross-coupling organo-halides or -triflates with organometallics.

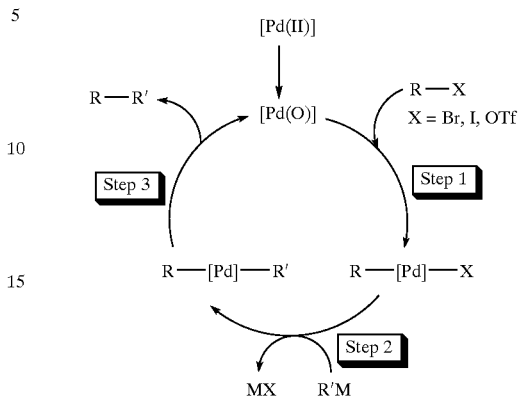

The mechanisms of both the oxidative addition and the reductive elimination steps have been studied extensively. However, less is known about mechanism of the transmetallation step. This method may be used with a large range of organometallic reagents, including tin, boron, and silicon. However, the alkenyltins have been the most widely used. Various organotin reagents will undergo transmetallation in a cross-coupling reaction with various organohalides (R—X, where X=Cl or I) and triflates (R—X, where X=OSO$_2$CF$_3$) (scheme 3). However, the organotin reagents have problems due to their inherent toxicity, and their sensitivity to light, air, and water.

Scheme 3.
General scheme for the Stille coupling.

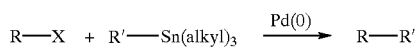

Organoboronic acids have also been used for transmetallation, in the so-called Suzuki coupling reaction (scheme 4). These reagents provide good yields of coupled products, and do not require special precautions due to their thermal stability and tolerance of water and oxygen. Disadvantages of organoboron reagents include their limited availability, their incompatibility with non-polar organic solvents, difficulties in purification, and lack of general utility in multi-step organic syntheses. Boronic acids tend to be less stable than silanes, and are considerably harder to purify.

Scheme 4.
General scheme for the Suzuki coupling.

Organosilanes are a third group of organometallic compounds that have been used in palladium cross-coupling reactions. Organosilicon compounds have been used as versatile reagents and as protecting groups in many organic syntheses. In addition to their synthetic utility, many silicon compounds are readily available, or are easily synthesized, providing a variety of structural variants as needed for particular reactions. Furthermore, organosilanes are compatible with most organic solvents. One drawback of organosilicon reagents for cross-coupling reactions has been the relatively low reactivity of most silane derivatives. One approach to overcoming this obstacle is to activate organosilanes toward transmetallation with palladium reagents (scheme 5). This strategy uses two approaches to enhance transmetallation reactivity: first, polarization of the Si—C bond by one or more fluorine (or chlorine) ligands on the silicon creates a better carbon nucleophile; and second, an in situ fluoride ion activator produces a more reactive pentacoordinate siliconate, which in turn also increases polarization of the Si—C bond. The organosilane cross-coupling reaction is compatible with a number of functional groups on the reacting species, including esters, aldehydes, ketones, alcohols, and nitrites. These reactions often require specialty halosilanes such as $RSiF_2Me$ or $RSiFMe_2$, employ less "user friendly" solvents such as DMF or THF, use harsh or specialized activators such as TBAF or TASF (tris(diethylamino)sulfonium difluorotrimethylsilicate), require relatively high temperatures (e.g. 100° C.), and often use air-sensitive palladium catalysts such as $(\eta^3-C_3H_5PdCl)_2$. Furthermore, the specialty halosilanes typically used in these reactions are not widely available, nor often used in multi-step organic syntheses, due to their reactivity and the difficulty of purifying them.

Scheme 5.
Fluoride activated Pd(0) catalyzed cross-coupling using organosilanes.

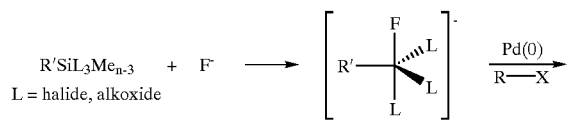

Most work in palladium-catalyzed cross-coupling reactions has focused on the choice of the organometallic compound. However, oxidative addition in the first step of the catalytic cycle (scheme 2) is equally important, and is often the rate-determining step. Most oxidative additions have used arylhalides (ArI, ArBr, ArCl). However, the appropriate arylhalide is not always readily available, nor easy to synthesize. Aryl and vinyl triflates have been used to cross-couple with organosilanes, allowing a wider variety and more readily available source of reagents for oxidative addition. However, the results have been unpredictable, giving better yields for some reactions and worse for others. It is noteworthy that the triflates are not reactive with trimethylsilane derivatives. Other alternatives such as O-arylcarbamates, arylsulfones, and arylmesylates have been investigated for oxidative addition in cross-coupling reactions; however, the first two are limited to Grignard reagents and require harsh reaction conditions, while arylmesylates give good yields for Ni-catalyzed reactions with boronic acids.

On the other hand, aryldiazonium tetrafluoroborate salts have been reported to be superior reagents in Heck reactions and Suzuki couplings. Aryldiazonium reagents are relatively easy to use in that they are not particularly sensitive to water, air, or light, and they can be used with protic solvents. The diazonium salts offer synthetic advantages over the halides and triflates since they furnish an excellent nucleofuge ($N_2$) which results from an essentially irreversible oxidative addition. Furthermore, diazonium salts are easily synthesized from a wide variety of available arylamine starting materials, and arylamines are much less expensive than aryl halides. Environmental considerations are also improved with diazonium salts since the nitrogen leaving group is inert and non-toxic.

Trimethylvinylsilane and other alkenylsilanes have been coupled to aryldiazonium salts using bis(dibenzylideneacetone)palladium(O) $(Pd(dba)_2)$ as a catalyst. This reaction exhibits a loss of regioselectivity, suggesting an addition-elimination mechanism that is essentially similar to the Heck reaction. It has been suggested that a putative intermediate, $Ar[Pd]^+BF_4^-$, adds to the alkene with syn-stereochemistry, followed by either (1) elimination to directly form the ipso substituted product, or (2) palladium transposition followed by elimination to give the cine product. See scheme 6. These mechanisms differ from the transmetallation reaction mechanisms previously proposed for other reactions of organosilicon compounds with palladium complexes.

Scheme 6.
Cross-coupling of an aryldiazonium salt with E and Z β-styrylsilane.

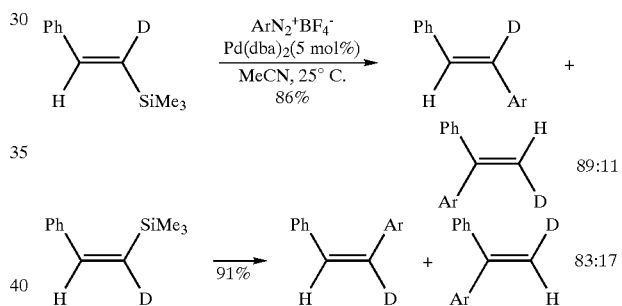

To synthesize stilbene derivatives, vinyltrimethylsilane reacts twice with iodophenyldiazonium tetrafluoroborate to give the bis(iodo-phenyl)stilbene. It has been reported that the second coupling reaction proceeds faster than the first. The product formed has been attributed to two sequential Heck reactions.

T. Hiyama, "Organosilicon compounds in cross-coupling reactions," pp. 421–453 in F. Diederich et al. (Eds.), *Metal-Catalyzed Cross-Coupling Reactions* (Wiley-VCH Verlag 1998) gives a review of organosilane cross-coupling reactions.

K. Kikukawa et al., "Reaction of diazonium salts with transition Metals. IX. Reaction of vinyltrimethylsilane with arenediazonium tetrafluoroborates under palladium(0) catalysis," *J. Organomet. Chem.*, vol. 270, pp. 277–282 (1984) discloses the cross-coupling of several arenediazonium tetrafluoroborates with vinyltrimethylsilane in the presence of palladium(0), to produce substituted styrene products.

K. Ikenaga et al., "Reaction of diazonium salts with transition metals. Part 11. Palladium-catalyzed aryldesilylation of alkenylsilanes by arenediazonium salts," *J. Chem. Soc. Perkin Trans.* 1986, pp. 1959–1964 discloses the palladium-catalyzed cross-coupling of various alkenylsilanes with various diazonium salts.

Y. Hatanaka et al., "Selective synthesis of unsymmetrical biaryls via palladium-catalyzed cross-coupling of arylfluorosilanes with aryl iodides," *Chem. Lett* 1989, pp. 1711–1714 discloses cross-coupling of arylfluorosilanes with aryl iodides in the presence of a palladium catalyst. The authors reported that in their system, "tetraorganosilanes like $PhSiMe_3$ and $Ph_4Si$ failed to give appreciable amounts of the coupled product 2 and produced instead biphenyl arising from the homo-coupling of phenylsilanes." Id. at p. 1713.

I have discovered a new reaction, in which palladium catalyzes the cross-coupling of an aryldiazonium salt with an arylsilane. A typical reaction is shown in scheme 7. New reactions that are user friendly and environmentally friendly are now possible, including some cross-couplings that could not be achieved using prior cross-coupling Methods. For example, to the inventor's knowledge, there have been no previous reports of successful cross-coupling of aryl palladium species with phenyltrimethylsilane, even in the presence of fluorine. Such reactions include the successful cross-coupling of two different aromatic reagents. The organosilanes that may be cross-coupled with aryldiazonium salts include, for example, Ar'—Si(L)$_3$, where Ar'=aryl, where L=$CH_3$, $OCH_3$, F, Cl, R, or OR, and where R denotes $C_2$–$C_5$ alkyl.

Scheme 7.
Palladium catalyzed aryldiazonium-organosilane cross-coupling reaction.

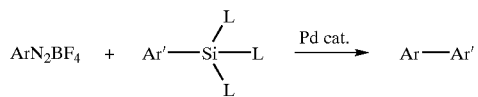

Although $ArN_2BF_4$ is a preferred reagent, other diazonium salts may be used in lieu of $ArN_2BF_4$. More generally, the reaction of scheme 7 may be conducted using a diazonium salt $ArN_2^+X^-$, where $X^-$ is a monovalent anion. Typical examples of X include $BF_4$, Cl, F, $SO_3CH_3$, $CO_2CH_3$, $PF_6$, $CO_2CH_3$, and $ClO_4$.

EXAMPLE 1

In proof-of-concept experiments, biphenyl reaction products have been successfully produced by the palladium-catalyzed cross-coupling of various arylsilanes with various aryldiazonium salts. The first such reaction attempted was that between phenyltrimethoxysilane and 4-methylphenyl diazonium tetrafluoroborate salt in the presence of palladium acetate in methanol. None of the desired biphenyl product was observed. Surprisingly, switching from palladium acetate to palladium chloride as a catalyst gave 20–48% product yields at room temperature, depending on the time of reaction. (scheme 8).

Scheme 8.
First example of palladium catalyzed cross-coupling of an aryldiazonium salt with an organosilane reagent.

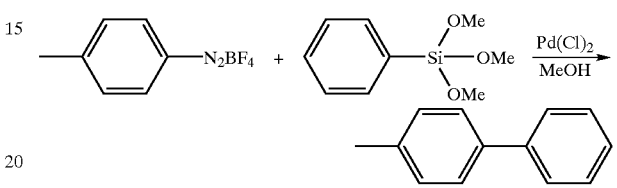

When the palladium chloride-catalyzed reaction was attempted in the solvents DMF and THF, however, no biphenyl reaction product was seen. This result may be attributed to the ability of methanol to reduce Pd(II) to Pd(0) by a reductive hydride elimination. This mechanism is supported by the observation that adding five equivalents of methanol to the DMF and THF reactions did result in the desired biphenyl product, albeit in low yield.

EXAMPLES 2–8

Initial optimization studies on time and temperature of the reaction gave the experimental results shown in Table 1. The general reaction conditions for the reactions shown in Table 1 were the following: To a suspension of the aryldiazonium salt (2.5 mmol) in 10.0 mL methanol was added the organosilane (2.5 mmol) and palladium chloride (0.25 mmol). The mixture was stirred under reflux for 4 hours, and the resulting reddish-brown solution was transferred to a separatory funnel. To the separatory funnel was added 30 mL $H_2O$, and the mixture was extracted twice with 30 mL $Et_2O$, and twice with 30 mL $CHCl_3$. The organic layers were then combined and dried over $MgSO_4$. The product was purified from the residue by flash chromatography (40 mm, 30 cm, 0–10% EtOAc/hexane).

TABLE 1

Cross-coupling phenyltrimethoxysilane with various aryldiazonium salts.

| Diazonium Salt | Organotrimethoxysilane | Equiv. Diazonium Salt | Equiv. Organosilane | Yield (%) |
|---|---|---|---|---|
| ⟨⟩—$N_2BF_4$ (with methyl) | ⟨⟩—$Si(OMe)_3$ | 1 | 1 | 30 |

TABLE 1-continued

Cross-coupling phenyltrimethoxysilane with various aryldiazonium salts.

| Diazonium Salt | Organotri-methoxysilane | Equiv. Diazonium Salt | Equiv. Organosilane | Yield (%) |
|---|---|---|---|---|
| 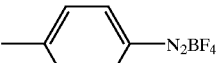 | 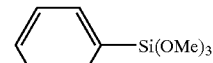 | 1 | 2 | 60 |
| 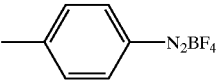 | 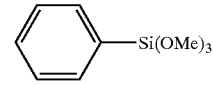 | 1 | 3 | 64 |
| 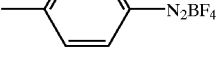 | 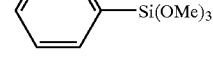 | 2 | 1 | 57 |
| 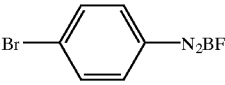 | 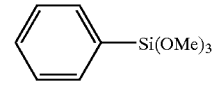 | 1 | 1 | 68 |
| 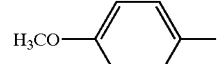 | 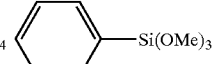 | 1 | 1 | 22 |
| 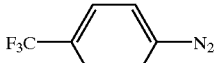 | 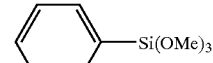 | 1 | 1 | 42 |

EXAMPLES 9 AND 10

The reaction also successfully cross-coupled the diazonium salt with phenyltrimethylsilane; results are shown in Table 2, reporting results for experiments that were otherwise conducted in accordance with the protocol given above for Table 1.

TABLE 2

Cross-coupling phenyltrimethylsilane with aryldiazonium salts.

| Diazonium Salt | Organotri-methylsilane | Equiv. Diazonium Salt | Equiv. Organo-trimethylsilane | Yield (%) |
|---|---|---|---|---|
| 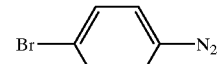 | 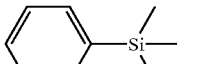 | 1 | 1 | 89 |
| 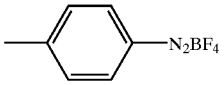 | 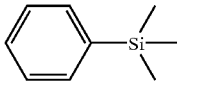 | 1 | 1 | 22 |

The palladium chloride catalyst appeared to work best with alcoholic or aqueous solvents. This combination of catalyst and solvent is advantageous. On the catalyst side, palladium chloride is readily available commercially, is a relatively inexpensive form of palladium catalyst, and requires no special handling since it is not sensitive to air, water, or light. On the solvent side, water or an alcohol such as methanol or ethanol is easy to use, is inexpensive, is easy to remove after reaction, and is environmentally friendly. The reaction products and byproducts tend, as a general rule, to be nontoxic. Thus this invention provides a relatively easy way to produce cross-coupled reaction products in an environmentally friendly manner.

In addition to the advantages provided by the solvent and catalyst, aryl-trimethylsilanes and aryldiazonium salts provide several advantages over other cross-coupling reagents. The trialkyl and trialkoxy substituted organosilane reagents are relatively safe and easy to handle. They are inexpensive, compatible with most solvents and other functionalities, and can often be purchased commercially and used as received. In fact, organosilanes are often used in multi-step synthesis strategies as protecting groups for latent functionality. These properties offer distinct advantages over organoborane reagents, since organoboranes are more highly reactive, have a low solubility in most organic solvents, and can be difficult to separate. The corresponding tin reagents are toxic, which limits their general use. The ability to transform the arylsilane functional groups into desired cross-coupled species in accordance with the present invention offers many advantages, especially in large scale or industrial applications.

The use of aryldiazonium salts allows for a wide array of possible reagents. The aryldiazonium salts may, for example, be obtained from their amine counterparts, which are often readily available commercially, or which may be easily synthesized by any of several methods known in the art. Once prepared, the aryidiazonium salts may be stably stored at −20° C. under nitrogen for several months. Another alternative is the in situ preparation of arenediazonium salts directly from the corresponding amine. Such in situ preparation may increase the safety of the reaction by avoiding the synthesis and storage of potentially hazardous reagents, and would also provide an approach to cross-coupling reactions that is even simpler overall.

Yields for the reaction vary, depending on the particular reactants used. Even in a particular reaction with a relatively lower yield, the starting materials can usually be separated from the reaction products and byproducts fairly easily, and then re-used as ingredients in another reaction, improving the overall effective yield, and reducing environmental impact. Separations may be conducted by conventional separation means, e.g., chromatography, partitioning between solvents, recrystallization, etc.

Previous attempts to cross-couple phenyltrimethylsilane with arylhalides produced primarily unwanted byproducts, even when fluoride was added. See Hatanaka et al. (1989). However, the present invention permits such cross-coupling reactions in reasonable yields, without the need for added fluoride. Without wishing to bebound by this theory, it is believed that the observed increase in yield arises from a cationic palladium intermediate in a new mechanism that differs from cross-coupling mechanisms that have previously been described. The proposed new catalysis mechanism is shown in scheme 9. The cationic palladium intermediate Ar—Pd$^+$BF$_4^-$ from step 1 initiates the electrophilic attack of aryltrimethylsilane ipso to the silyl group (step 2), followed by silyl elimination (step 3) to achieve re-aromatization, and reductive elimination (step 4) to complete the cycle. Such an electrophilic aromatic addition has not previously been reported or proposed for any aryl-aryl cross-coupling reaction.

Scheme 9.
Proposed reaction mechanism for cross-coupling
aryldiazonium salts with aryltrimethylsilanes.

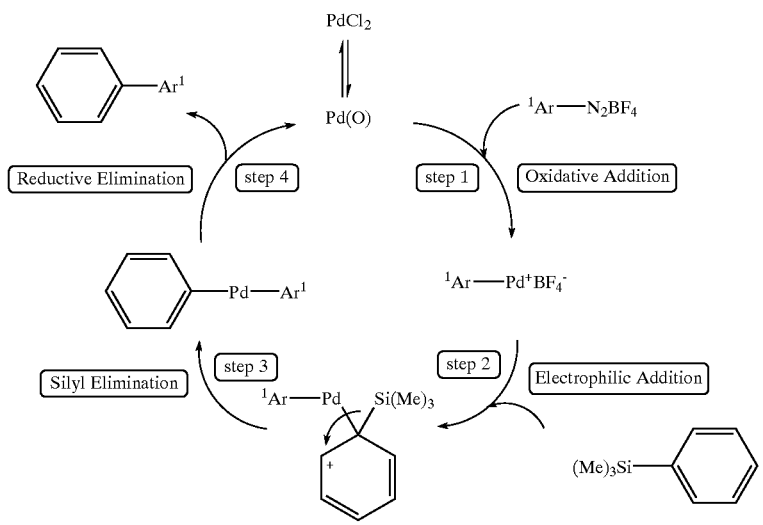

In addition to its applications in small molecule synthesis, the method of the present invention may also be used to synthesize macromolecular compounds that are not easily accessed with Suzuki-type couplings, while avoiding the toxicity of Stille-type couplings.

EXAMPLES 11–16
Coupling Aryltrimethylsilanes with Diazonium Salts

The most widely available silanes, and perhaps the most synthetically useful, are the trimethylsilyl derivatives. The novel method to transform trimethylsilanes to a desired carbon-carbon coupled product is an important and valuable tool for the synthesis of organic small molecules and polymers (scheme 10).

Scheme 10.
Cross-coupling of aryldiazonium salts with
organotrimethylsilanes.

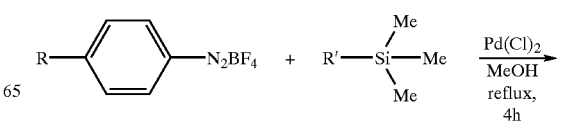

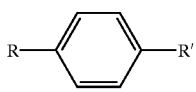

EXAMPLES 17–22
Coupling Phenyltrimethylsilane with Aryldiazonium Salts

All reaction conditions will initially be set at 10% palladium (II) chloride catalyst using refluxing methanol as solvent, to offer a fair comparison among various aryidiazonium and organosilane reagents; although conditions may thereafter be optimized for particular reactions. Table 3 shows typical cross-couplings that will be carried out with phenyltrimethylsilane (according to scheme 10). The reaction has now been carried out for two of the diazonium salts, with the yields as shown in Table 3.

prototype syntheses that have been conducted to date. Palladium (II) chloride has seldom previously been reported to be a viable catalyst by itself in coupling reactions, although it has sometimes been used in situ in conjunction with various activating ligands. Phosphine ligands will decompose aryldiazonium salts, precluding their use in the coupling strategies presented here. $Pd(OAc)_2$ has been used in both Suzuki and Heck type couplings. As discussed above, $Pd(OAc)_2$ initially showed no activity for methanolic cross coupling under the conditions used here; however, $Pd(OAc)_2$ will be investigated further with other solvents and coupling partners. Successful Suzuki couplings have previously been reported using $Pd(OAc)_2$. Successful cross-coupling results have also previously been reported using $Pd(dba)_2$, $Pd/C$, and $Pd_2(p-OAc)_2(P(o-tolyl)_3)_2$. Although our "standard" conditions are preferred both for cost and catalytic activity, these and other palladium catalysts may

TABLE 3

Cross-coupling phenyltrimethylsilane with various aryldiazonium salts.

| Diazonium Salt | Organotrimethyl-silane | Equiv. Diazonium Salt | Equiv. Organo-trimethylsilane | Yield (%) |
|---|---|---|---|---|
| $O_2N$—〈 〉—〈 〉— | 〈 〉—Si— | 1 | 1 | 47 |
| Br—〈 〉—$N_2BF_4$ | 〈 〉—Si— | 1 | 1 | 89 |
| —〈 〉—$N_2BF_4$ | 〈 〉—Si— | 1 | 1 | 22 |
| $H_3CO$—〈 〉—$N_2BF_4$ | 〈 〉—Si— | 1 | 1 | 26 |
| Et$_2$N—〈 〉—$N_2BF_4$ | 〈 〉—Si— | 1 | 1 | 11 |

EXAMPLE 23
Coupling of Aryidiazonium Salts with Derivatives of Trimethoxysilane, Trifluorosilane, and $Fluoro_n Methyl_{3-n}$ Silanes Aryl derivatives of the various silanes mentioned above will also be used in cross-coupling reactions in accordance with the present invention. For examples of some such reactions, namely several coupling various arenediazonium tetrafluoroborate salts with phenyltrimethoxysilane, see Table 1. The results found for the trimethoxy series were comparable to those for the two examples shown for the trimethylsilyl derivatives, although results for the trihalosilane derivatives may differ.

EXAMPLES 24–27
Other Palladium Catalysts

Palladium (II) chloride is a preferred catalyst for use in cross-couplings of the present invention, both because it is inexpensive and because it has worked well in the successful sometimes be useful in particular cross-coupling reactions in accordance with the present invention. Changing the catalyst can, for example, sometimes allow the use of alternative solvents, which broadens the scope of potential reactions and reagents, and which may in some cases improve yields.

As used in the specification and claims, an "aryl" group refers to a substituted or unsubstituted aromatic group, for example phenyl or substituted phenyl; and including heterocycles such as substituted and unsubstituted pyridyl; and including multi-ring systems such as substituted and unsubstituted biphenyl, naphthyl, and anthracenyl. If the aryl group is substituted, then possible substituents are such as those of skill in the art would select, and might include, for example, —F, —Cl, —Br, —I, —OH, —OR, $NR^1R^2$, —R, —$CF_3$, —$NO_2$, etc.; where R is substituted or unsubstituted $C_1$ to $C_5$ alkyl, and $R^1$ and $R^2$ are substituted or unsubstituted $C_1$ to $C_5$ alkyls that may be the same or different.

The complete disclosures of all references cited in this specification are hereby incorporated by reference. In the

I claim:

1. A method for cross-coupling an aryldiazonium salt and an arylsilane, comprising:
   (a) mixing the aryldiazonium salt and the arylsilane in the presence of a catalyst comprising palladium; wherein the aryldiazonium salt comprises $ArN_2^+X^-$, wherein $X^-$ is a monovalent anion; wherein Ar is aryl; and wherein the aryl silane comprises $Ar'—Si(L)_3$; wherein Ar' is aryl; Ar' and Ar may be the same or different; L is selected from the group consisting of $—CH_3$, $—OCH_3$, $—F$, $—Cl$, R, and $—OR$; wherein R denotes a $C_2$ to $C_5$ alkyl group; and wherein the three L substituents may be the same or different; and
   (b) reacting the aryldiazonium salt and the arylsilane for a time and at a temperature sufficient to allow formation of the cross-coupled product Ar—Ar'.

2. A method as recited in claim 1, wherein said reacting occurs in a solvent comprising water, methanol, or ethanol.

3. A method as recited in claim 1, wherein the catalyst comprises palladium (II).

4. A method as recited in claim 1, wherein the catalyst comprises palladium (II) chloride.

5. A method as recited in claim 1, wherein the catalyst consists essentially of palladium (II) chloride.

6. A method as recited in claim 1, additionally comprising the step of recovering the cross-coupled product Ar—Ar' from the reaction mixture.

7. A method as recited in claim 1, wherein X is selected from the group consisting of $BF_4$, Cl, F, $SO_3CH_3$, $CO_2CH_3$, $PF_6$, $ClO_2CH_3$, and $ClO_4$.

8. A method as recited in claim 1, wherein the reaction mixture is essentially free of fluoride.

9. A method as recited in claim 1, wherein X is $BF_4$, and wherein the reaction mixture is essentially free of fluoride from any source other than the $BF_4^-$ anion.

* * * * *